US009506912B2

(12) United States Patent
Yanik et al.

(10) Patent No.: US 9,506,912 B2
(45) Date of Patent: *Nov. 29, 2016

(54) HIGH-THROUGHPUT PLATFORM FOR IN-VIVO SUB-CELLULAR SCREENS ON VERTEBRATE LARVAE

(71) Applicant: Massachusetts Institute of Technology, Cambridge, MA (US)

(72) Inventors: Mehmet F. Yanik, Watertown, MA (US); Steven C. Wasserman, Concord, MA (US); Tsung-Yao Chang, Cambridge, MA (US); Cody L. Gilleland, Cambridge, MA (US); Carlos Pardo, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 270 days.

This patent is subject to a terminal disclaimer.

(21) Appl. No.: 14/518,070

(22) Filed: Oct. 20, 2014

(65) Prior Publication Data

US 2015/0045259 A1  Feb. 12, 2015

Related U.S. Application Data

(63) Continuation of application No. 12/713,263, filed on Feb. 26, 2010, now Pat. No. 8,865,630.

(51) Int. Cl.
*G01N 21/15* (2006.01)
*G01N 35/00* (2006.01)
(Continued)

(52) U.S. Cl.
CPC ...... *G01N 33/5088* (2013.01); *G01N 15/1475* (2013.01); *G01N 21/05* (2013.01); *G01N 35/00* (2013.01); *C40B 30/06* (2013.01);
(Continued)

(58) Field of Classification Search
CPC .. G01N 33/5088; G01N 21/05; G01N 35/00; G01N 15/1475; G01N 1/28; G01N 1/14; C40B 60/10; C40B 30/06
See application file for complete search history.

(56) References Cited

U.S. PATENT DOCUMENTS 8,228,499 B2   7/2012  Lippert et al.
2002/0025297 A1  2/2002  Frost et al.
(Continued)

FOREIGN PATENT DOCUMENTS

EP    1479759    11/2004
JP    05273203   10/1993
(Continued)

OTHER PUBLICATIONS

Funfak, Anette et al., "Micro Fluid Segment Technique for Screening and Development Studies on Dania Reiro Embryos", Lab on a Chip, vol. No. 9, US National Library of Medicine (NLM), Bethesda MD US NPL-57 Sep. 2007, pp. 1132-1138.
(Continued)

*Primary Examiner* — Jeremy C Flinders
(74) *Attorney, Agent, or Firm* — Strategic Patents, P.C.

(57) ABSTRACT

High throughput system for in vivo screens on vertebrate larvae. The system includes a source of vertebrate larvae in a liquid medium and loading tube means for aspirating a larva. A detector assembly is provided to differentiate passage of a larva from bubbles and/or debris. An imaging means is provided for both confocal imaging and wide-field fluorescence imaging of the larva. A laser is provided for optical manipulation of the larva.

20 Claims, 4 Drawing Sheets

(51) Int. Cl.
C40B 30/06 (2006.01)
C40B 60/10 (2006.01)
G01N 33/50 (2006.01)
G01N 21/05 (2006.01)
G01N 15/14 (2006.01)
G01N 1/14 (2006.01)
G01N 1/28 (2006.01)

(52) U.S. Cl.
CPC ............... *C40B 60/10* (2013.01); *G01N 1/14* (2013.01); *G01N 1/28* (2013.01)

(56) References Cited

U.S. PATENT DOCUMENTS

| | | |
|---|---|---|
| 2004/0092002 A1 | 5/2004 | Kim et al. |
| 2007/0187343 A1 | 8/2007 | Colucci et al. |
| 2007/0207450 A1 | 9/2007 | Rodgers et al. |
| 2010/0201784 A1 | 8/2010 | Lippert et al. |
| 2010/0239138 A1 | 9/2010 | Lippert et al. |
| 2011/0115895 A1 | 5/2011 | Huisken |
| 2011/0115896 A1 | 5/2011 | Doehring et al. |

FOREIGN PATENT DOCUMENTS

| | | |
|---|---|---|
| JP | 2001-133694 | 5/2001 |
| JP | 2008-119020 | 5/2008 |
| JP | 2009-186490 | 8/2009 |
| JP | 2009-204657 | 9/2009 |
| WO | WO-9820108 | 5/1998 |
| WO | WO-03052106 | 6/2003 |
| WO | WO-2004108270 | 12/2004 |
| WO | WO-2009079474 | 6/2009 |

OTHER PUBLICATIONS

Kokel, David et al., "Chemobehavioural phenomics and behaviour-based psychiatric drug discovery in the zebrafish", Briefings in Functional Genomics and Proteomics, vol. 7 No. 6. NPL-96 Sep. 10, 2008, pp. 483-490.

Pampaloni, Francesco et al., "The third dimension bridges the gap between cell culture and live tissue", Nature Reviews 1 Molecular Cell Biology, vol. 8, www.nature.com/reviews/molcellbio NPL-61 Oct. 2007, pp. 839-845.

King, Anthony, "Researchers Find Their Nemo", Cell 139, Elsevier Inc. NPL-90 Nov. 25, 2009, pp. 843-846.

McGrath, Patricia et al., "Zebrafish: A Predictive Model for Assessing Drug-Induced Toxicity", Drug Discovery Today (2008) NPL-85 May 2008, 8 Pages.

Lieschke, Graham J. et al., "Animal models of human disease: zebrafish swim into view", Nature Reviews Genetics, vol. 8 NPL-98 May 2007, pp. 353-367.

Bhatt, Dimple H. et al., "Cyclic AMP-Induced Repair of Zebrafish Spinal Circuits", www.sciencemag.org. Science, vol. 305 NPL-95 Jul. 9, 2004, pp. 254-258.

Vogt, Andreas, "Automated Image-Based Phenotypic Analysis in Zebrafish Embryos", Developmental Dynamics, vol. 238, Wiley-Liss, Inc. US NPL-58 Jan. 2009, pp. 656-663.

Zon, Leonard I. et al., "In Vivo Drug Discovery in the Zebrafish", Nature Reviews Drug Discovery, vol. 4 NPL-91 Jan. 2005, pp. 35-44.

Patton, E. Elizabeth et al., "The Art and Design of Genetic Screens: Zebrafish", Nature Reviews Genetics; vol. 2 NPL-89 Dec. 2001, 11 pages.

Amatruda, James F. et al., "Zebrafish as a cancer model system", Cancer Cell: vol. I NPL-88 Apr. 2002, pp. 229-331.

Wen, Lu et al., "Visualization of monoaminergic neurons and neurotoxicity of MPTP in live transgenic zebrafish", Developmental Biology, vol. 314 NPL-100 2008, pp. 84-92.

Buckley, Clare E. et al., "Zebrafish Myelination: A Transparent Model for Remyelination?", Disease Models & Mechanisms NPL-87 2008, pp. 221-228.

Barros, T.P. et al., "Zebrafish: an emerging technology for in vivo pharmacological assessment to identify potential safety liabilities in early drug discovery", British Journal of Pharmacology (2008) vol. 154 NPL-84 2008, pp. 1400-1413.

Lee, Jin-Woo et al., "Differentiation of Mouse P19 Embryonic Carcinoma Stem Cells Injected into an Empty Zebrafish Egg Chorion in a Microfluidic Device", Bioscience, Biotechnology, and Biochemistry, vol. 70 (6) 2006, pp. 1325-1330.

Den Hertog, Jeroen, "Chemical Genetics: Drug Screens in Zebrafish", Bioscience Reports, vol. 25, Nos. 5/6 2005, pp. 289-297.

Langheinrich, Ulrike, "Zebrafish: a new model on the pharmaceutical catwalk", BioEssays vol. 25 (9), Wiley Periodicals, Inc 2003, pp. 904-912.

Rubinstein, Amy L., "Zebrafish: From disease modeling to drug discovery", Current Opinion in Drug Discovery & Development 6(2) 2003, pp. 218-223.

Shin, Jordan T., "From Zebrafish to Human: Modular Medical Models", Annual Review of Genomics and Human Genetics, vol. 3 2002, pp. 311-340.

Karlsson, Johnny et al., "Generating Transparent Zebrafish: A Refined Method to Improve Detection of Gene Expression During Embryonic Development", Marine Biotechnology, vol. 3, Springer-Verlag New York, Inc. 2001, pp. 522-527.

Zottoli, Steven J. et al., "The Mauthner Cell: What Has It Taught Us?", The Neuroscientist 2000, pp. 26-38.

Henriksen, G.H. et al., "Laser-assisted patch clamping: a methodology", Pflilgers Arch—European Journal of Physiology (1997), Springer Verlag, Berlin DE vol. 433 Jan. 1, 1997, pp. 832-841.

Wang, Wenhui H. et al., "High-Throughput Automated Injection of Individual Biological Cells", IEEE Transactions on Automation Science and Engineering. vol. 6. No. 2, Apr. 1, 2009, pp. 209-219.

USPTO, "U.S. Appl. No. 12/713,263 Non-Final Office Action mailed Feb. 22, 2013", 23 Pages.

USPTO, "U.S. Appl. No. 12/713,263 Final Office Action mailed Jul. 15, 2013", 13 pages.

USPTO, "U.S. Appl. No. 12/713,263 Notice of Allowance mailed Aug. 19, 2014", 15 pages.

EPO, "EP Application Serial No. 11701928.1, European Office Action mailed Dec. 18, 2013", 8 Pages.

JPO, "Japanese Application No. 2012-555009 Second Office Action", Japanese and English Translations, 5 Pages, Jan. 2014.

JPO, "JP Application No. 2012-555009 Office Action mailed Jan. 28, 2014", 19 pages.

ISA, "PCT Application No. PCT/US11/22354 International Search Report and Written Opinion", 12 pages, Oct. 2011.

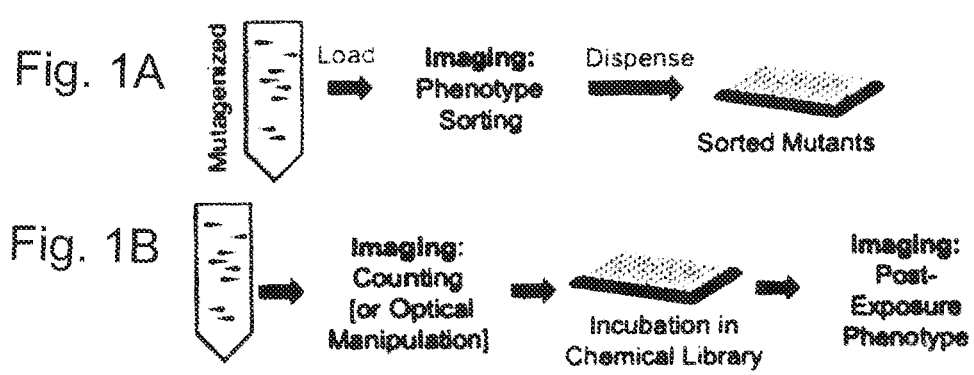

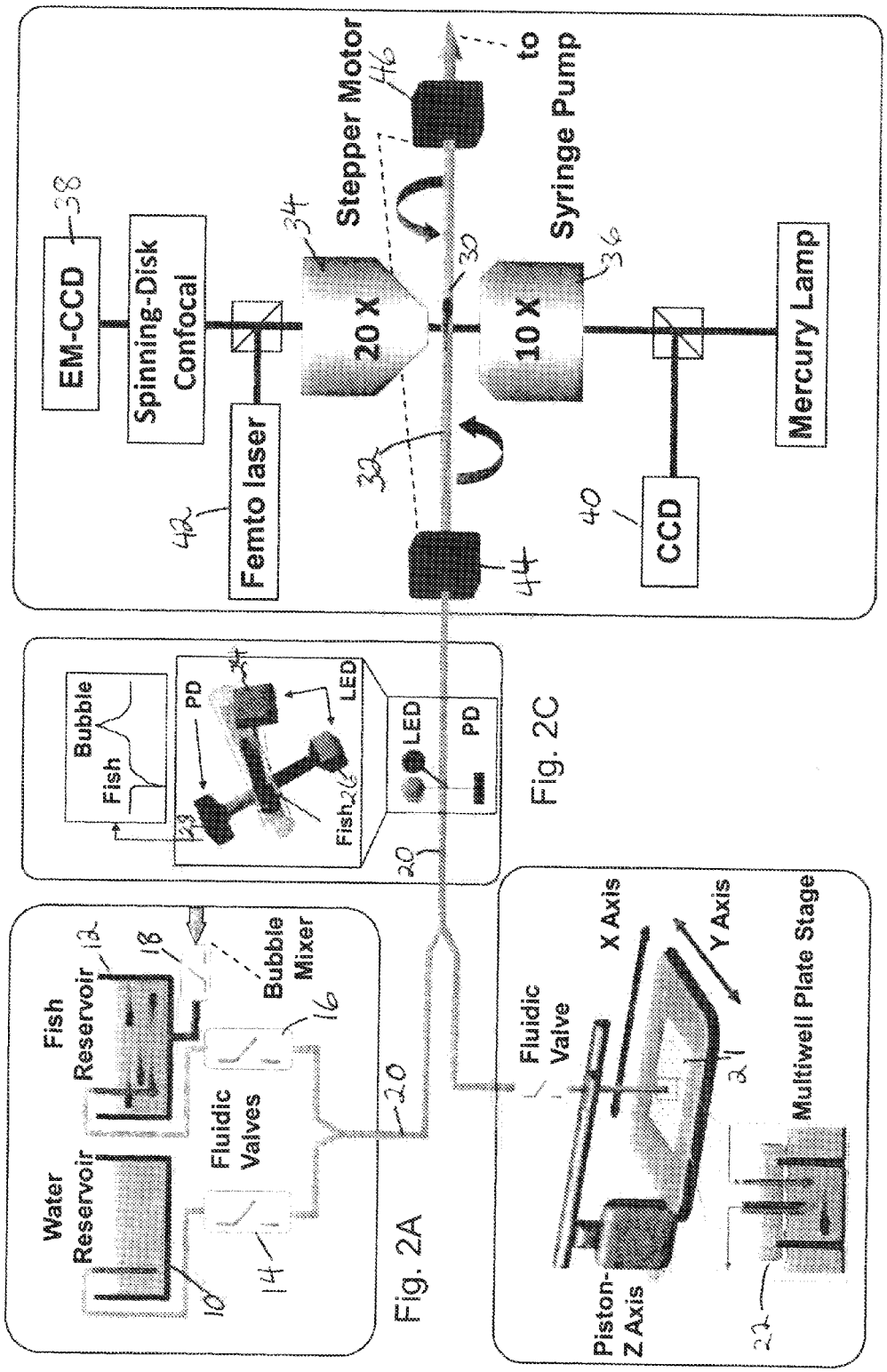

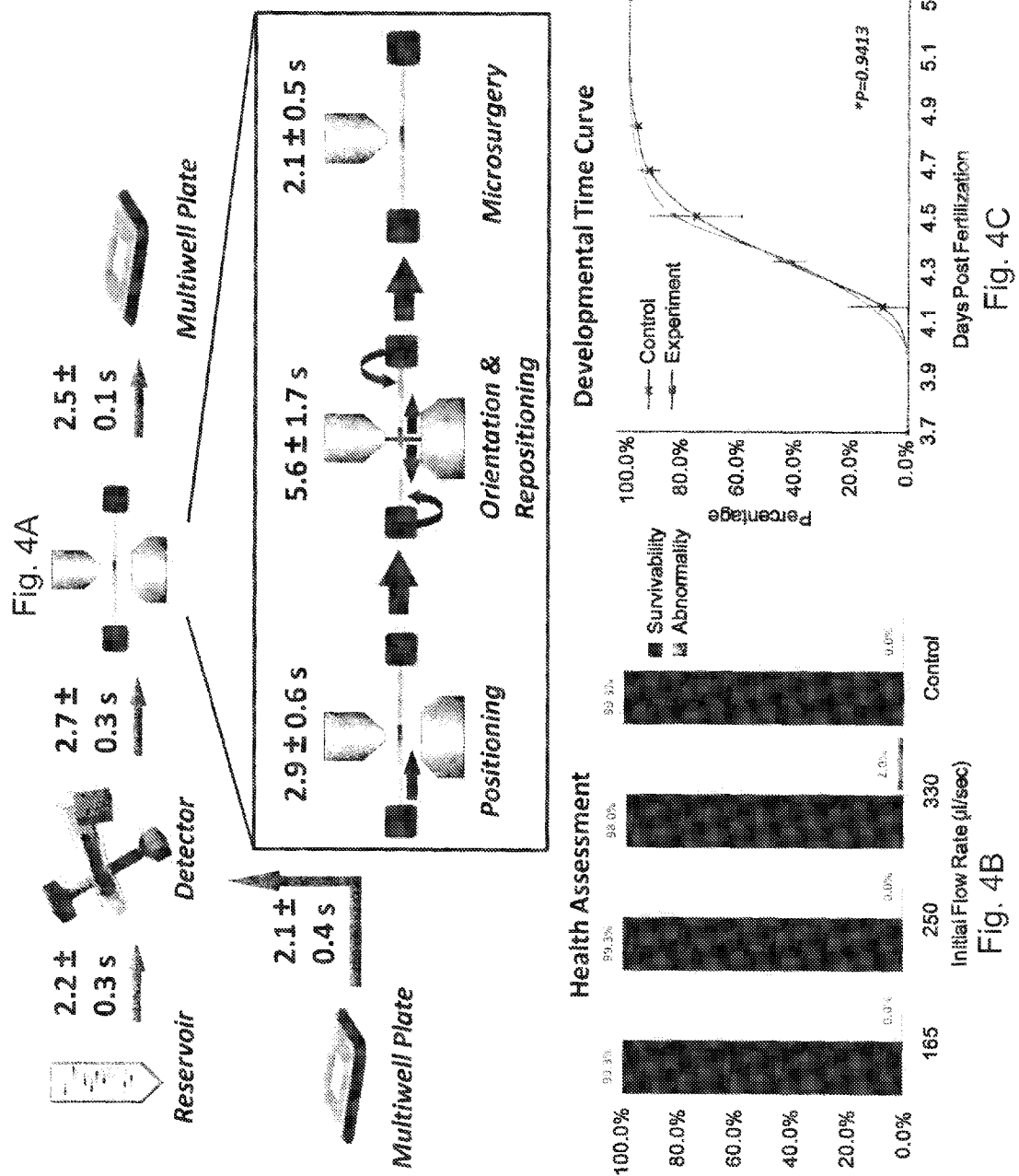

HIGH-THROUGHPUT PLATFORM FOR IN-VIVO SUB-CELLULAR SCREENS ON VERTEBRATE LARVAE

CROSS-REFERENCE TO RELATED APPLICATIONS

This application is a continuation of U.S. patent application Ser. No. 12/713,263 filed Feb. 26, 2010, which is hereby incorporated by reference in its entirety.

BACKGROUND OF THE INVENTION

This invention relates to a high throughput screening platform and more particularly to a high throughput platform capable of in vivo genetic and chemical screens on specimen organisms such as zebrafish larvae and other teleosts.

Small animal models such as zebrafish (*Danio Rerio*) facilitate the study of complex processes on a large scale that cannot be replicated in vitro such as: organ development; neural degeneration and regeneration; stem cell proliferation and migration; cardiovascular, immune, endocrine, and nervous system functions; infectious disease progression; pathogenesis; cancer progression; and tissue specificity and toxicity of drugs. Several desirable attributes of zebrafish have fueled its popularity, including the animal's small size, optical transparency, aquatic habitat, and simplicity of culture. Zebrafish models of several human diseases have been developed[1-11]. Superscript numbers refer to the references included herewith. The contents of all these references are incorporated herein by reference. Lead compounds discovered by screening chemical compound libraries for efficacy in zebrafish disease models have been useful for pharmaceutical development because of the high level of conservation of drug activity between mammals and zebrafish[12,13]. The availability of large numbers of mutant strains and genetic manipulations such as gene overexpression, knockdown, and silencing make zebrafish a powerful model for genetic studies and for identification of the cellular targets of new compounds[1,14,15]. The significant advantages of zebrafish have fueled exponential growth of its use in experimental investigations over the last two decades[1].

Several companies and academic labs are conducting genetic and compound screens on zebrafish larvae incubated in 96-well plates[1,2,4,12.] Because handling of zebrafish has been largely manual, typical high-content zebrafish screens are limited to only a few thousand compounds per week. Subcellular resolution assays require optical access to a specific region of the specimen for imaging or manipulation. Clear access is often impeded by intervening organs such as eyes and heart. Yolk and some organs exhibit significant autofluorescence. In addition, skin pigmentations can block the region of interest. Visualization of most of the regions requires orienting the zebrafish appropriately. However, current specimen orientation methods require embedding the sample in viscous media such as agar and/or manually rotating the fish with forceps. These processes are too slow and unreliable for high-throughput screens. In addition, specimens cannot be rapidly re-oriented once they are fixed, thus impeding visualization of organs from multiple angles. Examples of assays that require sample orientation and subcellular resolution imaging include in vivo monitoring of early tumor growth, neuronal degeneration, neurite regeneration, and stem cell proliferation and migration in tissues comprising the brain, eyes, heart, pancreas, kidneys, and liver.

SUMMARY OF THE INVENTION

In one aspect, the high throughput system of the invention for in vivo screens includes a source of specimen organisms in a liquid medium. Suitable specimen organisms include teleosts or other aquatic animals and embryos. A preferred teleost is zebrafish larvae. An automatic means is provided to load the specimen organisms from the source into a tube. An automatic detector detects passage of the specimen organisms through the tube. Also provided is an automatic means to position the specimen organism in the tube within the field-of-view of an imaging apparatus.

In a preferred embodiment, the larvae are zebrafish. It is preferred that the source of larvae be a reservoir or a multiwell plate. The reservoir may include a fish reservoir and a liquid reservoir. It is preferred that the multiwell plate be a 96 well plate and that it sits on an x-y position stage. In yet another preferred embodiment, the detector assembly includes two light emitting diodes and one high-speed photodiode arranged in transmission and reflection configurations. In an embodiment, the imaging means includes a pair of stepper motors for rotating a capillary tube to reorient a larva. The capillary tube may preferably be glass or Teflon.

In yet another embodiment, the imaging means includes a 20 power water-immersion objective lens for confocal imaging. The imaging means also includes an inverted 10 power objective lens for brightfield imaging. It is preferred that the imaging means include a cooled electron-multiplying CCD camera. It is preferred that the laser be a femtosecond laser. The femtosecond second laser is selected to generate a beam suitable for microsurgery or ablation and/or photoactivation. The system disclosed herein may be used to perform genetic or chemical screens.

BRIEF DESCRIPTION OF THE DRAWING

FIGS. 1A and 1B are the schematic flow diagrams for chemical and genetic screens according to an embodiment of the invention.

FIGS. 2A-2D are schematic diagrams of the zebrafish screening platform disclosed herein.

FIGS. 4A-4C are illustrations showing a quantitative assessment of animal health.

DESCRIPTION OF THE PREFERRED EMBODIMENT

Figure 3A:
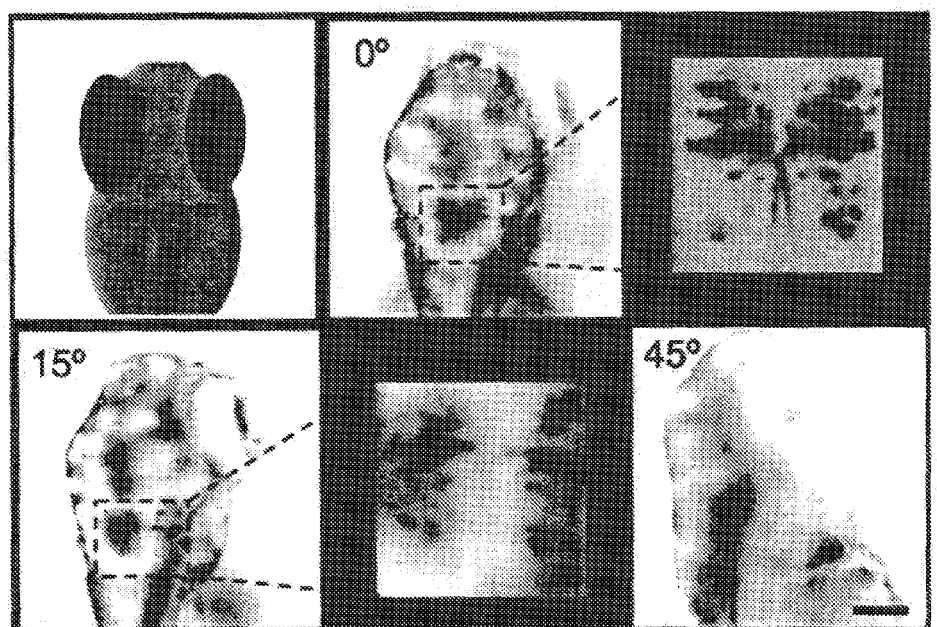
FIGS. 3A-3B are photomicrographs showing zebrafish orientation, imaging, femtosecond laser microsurgery and regeneration.

To facilitate a dramatic improvement in the throughput and complexity of zebrafish screens, we developed a platform for rapid manipulation of zebrafish larvae. Zebrafish larvae will be used herein to describe the invention. It is to be recognized that other teleosts and aquatic animals and embryos may be used and it is intended that other such specimen organisms be included within the term zebrafish larvae. The automated system allows both genetic and chemical screens, as shown in FIGS. 1A and B. For genetic screens, mutagenized animals are loaded from a reservoir to the imaging platform. After imaging, the mutants are sorted into multilevel plates by phenotype. For chemical screens, animals are loaded from a reservoir to the imaging platform which can be used either to count the number of animals and/or to perform optical manipulations such as laser microsurgery. The animals are then dispensed into multiwell plates containing chemicals to be tested. After incubation within chemicals, the animals are loaded back into the imaging platform to check phenotypes.

Examples of genetic and chemical screens that can be performed with the present invention include a chemical screen for organ regeneration searching for promoters of progenitor cells proliferation. This assay can be performed in multiple organs such as the liver, the kidneys, the pancreas, skeletal muscle, hair follicles and the central and peripheral nervous system. Another example is screens for inhibitory chemicals targeting tumorigenic cell proliferations in vivo. Yet another example is screens for protective chemicals that significantly reduce or inhibit cell hypotrophy or death in degenerative disease models such as Parkinson's Disease, Alzheimer's or Huntington's Disease. Screens to assess biological toxicity of drugs in multiple organs, such as in the liver, kidneys, pancreas, heart, hair cells and neurons in the central and peripheral nervous systems are contemplated. Genetic and chemical screens to study the differentiation and proliferation of different cell lineages and organogenesis by photoactivation of fluorescent reporter proteins as lineage tracers may also be preformed using the system of the invention disclosed herein.

The capability to work with standard multiwell plates is essential for handling and incubating large populations of zebrafish larvae, so the system was designed to automatically load specimens from and dispense them back into individual wells. The system also has the ability to load animals from reservoirs. After automatic loading, animals are positioned within the field-of-view (FOV) of an optical imaging and manipulation subsystem with high-speed confocal imaging and optical manipulation capabilities. Specimens can be repositioned and rotated on the fly, eliminating the need for manual handling and invasive chemical methods to suppress skin pigmentation such as phenylthiourea (PTU) treatment[16]. Furthermore, active control of specimen orientation permits the use of high numerical aperture (NA) objective lenses that require short working distances. High NA objectives collect more light, reduce background fluorescence, and diminish scattering and absorption by intervening tissue. Using our system, high-content subcellular-resolution screens are possible.

With reference now to FIG. 2A a liquid medium reservoir 10 and a fish reservoir 12 are controlled with fluidic valves 14 and 16. A bubble mixer 18 injects bubbles into the fish reservoir 12 to provide agitation. A syringe pump (not shown) allows fish larvae to be aspirated into a tube 20. After one animal enters the tube, the two computer-controlled valves 14 and 16 automatically switch the fluid source from the larvae reservoir 12 to a separate reservoir 10 containing fish medium to prevent loading of multiple fish.

In an alternative embodiment as shown in FIG. 2B, larvae are included in a multiwell plate 21 supported on an x-y position stage. The 2-axis stage positions a single well beneath a pneumatic piston that lowers the endpoints of two silicon tubes (loading and supply tubes with diameters of 1.0 and 0.2 mm, respectively) into the volume of the selected well. A silicone rubber block 22 seals a well surface to facilitate depressurization. The larva is aspirated through a loading tube while a supply tube simultaneously replenishes the fluid removed.

A zebrafish larva from either the fish reservoir 12 or from a well in the multiwell plate 21 passes through a detector section of the system as shown in FIG. 2C. The detector system automatically discerns the entry of larvae into the tube 20 from either the wells 21 or the reservoir 12 and includes two light emitting diodes 24 and 26 and a photodetector 28 positioned around the tube 20. The light emitting diode 26 is arranged so that its light is transmitted through a larva and received by the photodetector 28. The light emitting diode 24 is offset so that light reaching the photodetector 28 has been scattered. By simultaneously monitoring both the transmission and scattering signals, the system of the invention differentiates the passage of a larva from air bubbles and debris. To ensure recognition of the rapidly moving animals, the detector operates at a preferred sampling rate of 2 kHz.

A larva moves from the detector section shown in FIG. 2C into an image system shown in FIG. 2D. As shown in FIG. 2D, a larva 30 is located within the FOV in a Teflon capillary tube 32 having an inner diameter of approximately 800 μm. The capillary 32 is matched to the refractive index of water to prevent image distortion. The capillary tube 32 may be glass.

As shown in FIG. 2D, the optical imaging system includes two microscopes: one upright and the other inverted. The upright lens 34 is a 20× (NA=1.0) water-immersion objective lens for confocal imaging and an inverted 10× lens 36 is an air objective lens for brightfield imaging. A high-speed spinning-disk confocal head with a cooled electron-multiplying EM CCD camera is connected to the microscope's upright port for video frame rate confocal fluorescence imaging. The electron-multiplying CCD camera is element 38. A second CCD camera 40 is connected to an inverted port for detection and positioning of larvae. A femtosecond laser 42 provides a beam used for microsurgery or ablation and photoactivation or photostimulation and is directed to the upper beam path by a dichroic filter and focused on the sample through the 20× objective 34. Two stepper motors 44 and 46 are precisely controlled to rotate in opposite directions so as not to twist the capillary 32 thereby providing for accurate location of the larva 30.

A computer-controlled syringe pump (not shown) automatically controls coarse positioning of a larva inside the capillary tube 32 within the field of view of the optical subsystem of FIG. 2D. The capillary 32 is matched to the refractive index of water to prevent image distortion. Using images from a fast EMCCD camera, an automated image processing algorithm detects the entrance of a larva into the field of view and subsequently stops the syringe pump. After coarse positioning of the larva with the syringe pump, a 3-axis position stage automatically moves the capillary assembly to position the animal's head at the center of the camera's field of view via automated image processing as is known in the art.

The animals are oriented on-the-fly by a pair of stepper motors 44 and 46 that rotate the capillary 32. The motors 44 and 46 are mounted on a support structure with their shafts facing one another. The motors are driven by a microstep controller connected to a computer (not shown) which allows 0.2 degree steps at an angular velocity of up to 180 degrees per second. The entire motor and capillary assembly, plus a water filled imaging chamber in which the top objective is immersed, is mounted on the 3-axis motorized position stage. Thus, larvae can be arbitrarily positioned and oriented within the microscope's field of view with submicron accuracy. The imaging system allows simultaneous wide-field fluorescence imaging and high speed, high-resolution, spinning disk confocal microscopy. The imaging system may have two-photon imaging capability.

FIG. 3A shows an example set of confocal images of one specimen oriented at several angles to visualize the midline crossing of the Mauthner neuron axons[7]. The midline crossing is only visible when observed from the hindbrain (0° in the figure). At less favorable orientations, the structure is obscured. Images are shown additionally at 15° and 45°. The scale bar is 150 µm.

Figure 3B:
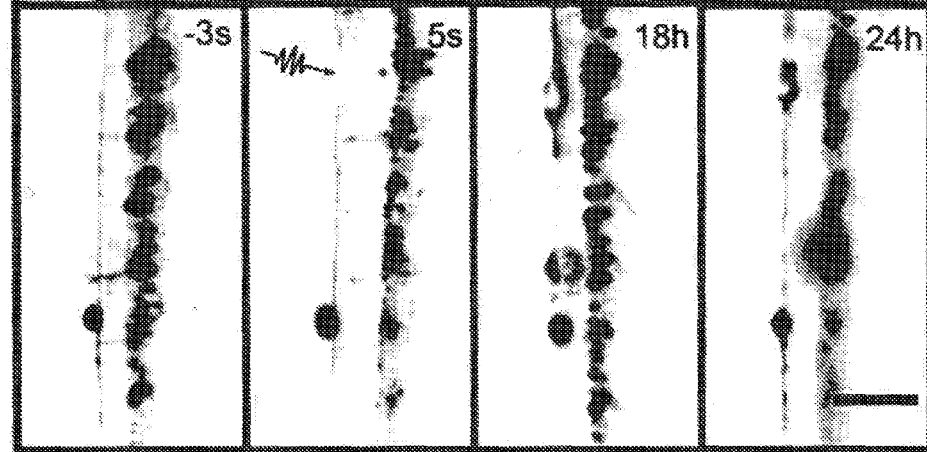

The system also incorporates a subcellular-precision, femtosecond laser stimulation capability. Combined with the precise automatic positioning and orientation capabilities of the system, the femtosecond laser 42 enables optical manipulations such as localized activation of fluorescent reporters and ion channels, uncaging of compounds, and laser microsurgery. FIG. 3B shows an example of how the system would be used to study neuronal regeneration following injury by laser microsurgery. Zebrafish have significant regenerative capacity, which makes them a powerful model for investigating regenerative mechanisms as well as for screening chemicals that enhance regeneration. Existing assays for injuring zebrafish using scalpels are too slow and invasive for reliable, large-scale studies of regeneration[18]. In the image, the lateral-neuron axon fiber bundle projecting along the trunk of a larva is visible when the larva is laterally oriented. Precise laser axotomy is achieved by focusing near infrared (NIR) femtosecond laser pulses (white arrow in FIG. 3B) as we previously demonstrated for study of neuronal regeneration in *C. elegans*[13]. At NIR wavelengths, the tissue is highly transparent; however, nonlinear absorption of photons at the focus of the ultra-short pulses allows micron-precision axon ablation without damaging surrounding tissue. The surgery is done semi-automatically in our system for highest throughput. The user selects a cell body by clicking on a graphical user interface. An algorithm estimates the distance from the cell body to the point of axotomy along the axon. The position stage automatically moves the axonal region to be axotomized to the focal spot of the laser 42. Femtosecond laser 42 pulses are then automatically delivered by opening an electro-optical laser shutter to perform the microsurgery. FIG. 3B also shows the regrown axonal fibers at 18 and 24 hours post-axotomy. The axon fiber is cut 850 µm distance from the soma using ultrashort laser pulses with 780 nm wavelength, 100 fs duration, 15 nj pulse energy, 80 MHz repetition rate and 10 ms long pulse train focused by a 20× NA=1.0 objective lens. Scale bar is 75 µm.

After imaging and manipulation, larvae are dispensed into multiwell plates for further incubation by executing the loading process in reverse. The dispensed solution volume is hydraulically controlled to a precision greater than 10 µL. A complete cycle consisting of loading, positioning, rotating, sub-cellular resolution confocal imaging, and dispensing an animal takes less than 16 seconds (FIG. 4A). Performed manually, similar assays require about 10 minutes, and the failure rate is much higher.

Zebrafish larvae are delicate; their yolks are particularly susceptible to indelicate handling. We tested alternative methodologies and flow rates to develop a minimally injurious system. The most significant damage to the larvae occurs during its entry from the reservoir 12 or multiwell plate 21 into the loading tube 20 at high aspiration rates. Since high aspiration rates are necessary for acceptable throughput, the flow is started at a low initial rate before an animal enters the loading tube to reduce the chance of injury, and the rate is then increased at a constant acceleration of 42 µl/s² until a larva is detected by the photodetector (FIG. 2C). The maximum flow rate is limited to 330 µl/s. At this maximum flow rate, no injury to larvae occurs if the larva is within the tubing. Once a larva is detected inside the capillary 32, the control software automatically decreases the aspiration rate to 83 µl/s to allow automated recognition of the larva by the camera 38. FIG. 4B shows the results for 450 larvae screened by the system at three different initial aspiration rates. After 36 hours, larval health was assessed by visual confirmation of normal heartbeat, morphology, and reflex response to touch and light stimuli. At the highest initial flow rate (330 µl/s), 2.0% of the animals exhibited a morphological abnormality. The abnormality criteria included lordosis, kyphosis, scoliosis and craniofacial abnormalities[19]. Post manipulation developmental delay was measured by monitoring the time of appearance of the swimming bladder. As shown in FIG. 4C, there was no significant (P=0.94) difference between development of larvae that were manipulated by the system and control animals, even at the highest flow rates. Furthermore, when operating at a slightly slower loading rate (increasing the cycle time approximately by 1 second), the system had no effect on survivability.

We have demonstrated a high-throughput platform for manipulating a specimen organism with cellular-resolution imaging and surgery capabilities, enabling complex in vivo high-throughput assays such as neuronal regeneration. The platform can be used for both forward and reverse genetic screens, as well as for chemical screens. The platform automatically loads and dispenses animals from multiwell plates, which is crucial for large-scale incubation of zebrafish. It is capable of orienting animals on-the-fly with sub-degree precision and therefore allowing visualization and manipulation of superficial and deep structures that are otherwise inaccessible in existing high-throughput screens. The entire process of loading, positioning, orienting, imaging, laser micromanipulation, and dispensing of animals takes place within 18 seconds, an improvement of about two orders of magnitude over existing methods. Screening hundreds of animals demonstrated that our system works non-invasively and reliably in the presence of artifacts such as air bubbles and debris in the medium. Thus, our platform can significantly accelerate the throughput of sophisticated assays on vertebrates.

It is recognized that modifications and variations of the invention will be apparent to those of ordinary skill in the art, and it is intended that all such modifications and variations be included within the scope of the appended claims.

REFERENCES

1. Zon, L. I., Peterson, R. T., In vivo drug discovery in the zebrafish. *Nat Rev Drug Discovery* 4(1), 35-44 (2005).

2. Amatruda, J. F., Shepard, J. L., Stern, H. M., Zon, L. I., Zebrafish as a cancer model system. *Cancer Cell* 1(3), 229-31 (2002).

3. Rubinstein, A. L., Zebrafish: from disease modeling to drug discovery. *Curr Opin Drug Discov Devel.* 6(2), 218-23 (2003).

4. Kokel, D., Peterson, R. T., Chemobehavioural phenomics and behaviour-based psychiatric drug discovery in the zebrafish. *Brief Funct Genomic Proteomic.* 7(6), 483-90 (2008).

5. Langheinrich, U., Zebrafish: a new model on the pharmaceutical catwalk. *Bioessays* 25(9), 904-12 (2003).

6. Banos, T. P., Alderton, W. K., Reynolds, H. M., Roach, A. G., Berghmans, S., Zebrafish: an emerging technology for in vivo pharmacological assessment to identify potential safety liabilities in early drug discovery. *Br J Pharmacol.* 154(7), 1400-13 (2008).

7. den Hertog, J., Chemical genetics: Drug screens in Zebrafish. *Biosci Rep.* 25(5-6), 289-97 (2005).

8. Lee, J. W., Na, D. S., Kang, J. Y., Lee, S. H., Ju, B. K., Differentiation of mouse p19 embryonic carcinoma stem cells injected into an empty zebrafish egg chorion in a microfluidic device. *Biosci Biotechnol Biochem.* 70(6), 1325-30 (2006).

9. Buckley et al. Zebrafish myelination: a transparent model for remyelination?. *Disease Models & Mechanisms* 1, 221-228 (2008).

10. McGrath, P., Li, C., Zebrafish: a predictive model for assessing drug-induced toxicity. *Drug Discovery Today* 13(9-10), 394-401 (2008).

11. Wen et al. Visualization of monoaminergic neurons and neurotoxicity of MPTP in live transgenic zebrafish. *Developmental Biology* 314, 84-92 (2007).

12. King, A., Researchers find their Nemo. *Cell* 139(5), 843-846, (2009)

13. Shin, J. T., Fishman, M. C., From Zebrafish to human: modular medical models. *Annu. Rev. Genomics. Hum. Genet.* 3, 311-40 (2002).

14. Lieschke, G. J., Currie, P. D., Animal models of human disease: zebrafish swim into view. *Nature Genetics* 8, 353-367 (2007).

15. Patton, E. E., Zon. L. I., The art and design of genetic screens: zebrafish, *Nature Genetics* 2, 956-966 (2001).

16. Karlsson, J,. Hofsten, J. V., Olsson, P. E., Generating Transparent Zebrafish: A Refined Method to Improve Detection of Gene Expression During Embryonic Development. *Marine Biotech.* 3, 522-7 (2001).

17. Zottoli, S. J., Faber, D. S., The Mauthner Cell: What Has it Taught us?. *The Neuroscientist* 6(1), 26-38 (2000).

18. Bhatt D. H., Otto S. J., Depoister B, Fetcho J. R., Cyclic AMP-induced repair of zebrafish spinal circuits. *Science* 305(5681), 254-8 (2004).

19. Hutchinson T. H., Williams T. D., Culturing of fathead minnow larvae for aquatic toxicity testing: an observational note, *Environ. Toxico.l Chem.* 13, 665-669 (1993).

What is claimed is:

1. A high-throughput system for in vivo screens comprising:
   a source of a specimen organism in a liquid medium;
   a pump configured to load the specimen organism in the liquid medium into a transparent tube;
   an automatic optical means to position the specimen organism in the transparent tube within a field-of-view of an imaging apparatus for microscopy through the transparent tube; and
   a motor and capillary assembly operable to rotate the transparent tube, thereby rotating the specimen organism within the field-of-view of the imaging apparatus.

2. The system of claim 1 wherein the specimen organism is a teleost.

3. The system of claim 2 wherein the teleost is zebrafish.

4. The system of claim 1 wherein the specimen organism is transgenic.

5. The system of claim 1 wherein the source is a reservoir containing a plurality of specimen organisms.

6. The system of claim 1 wherein the source includes a multiwell plate containing a plurality of specimen organisms.

7. The system of claim 6 wherein the source can be switched between the source and a liquid supply.

8. The system of claim 6 wherein a tube assembly is positioned on the multiwell plate by a position stage.

9. The system of claim 8 wherein the tube assembly includes an injection tube to inject fluid and an aspiration tube to aspirate one of the plurality of specimen organisms from the multiwell plate.

10. The system of claim 8 wherein the tube assembly and multiwell plate can be sealed.

11. The system of claim 1 wherein the system includes an automatic detector to detect entry of the specimen into a tube connecting the liquid medium to the transparent tube, the automatic detector including one or more light sources and one or more light detectors arranged in transmission and/or reflection configurations about the tube.

12. The system of claim 11 wherein the automatic detector differentiates air bubbles and/or debris from the specimen.

13. The system of claim 1 wherein the transparent tube includes a portion that is a glass or quartz or transparent polymer capillary within the field-of-view of the imaging apparatus.

14. The system of claim 13 wherein the transparent tube is index matched to the liquid medium.

15. The system of claim 1 wherein the imaging apparatus simultaneously images through two objective lenses.

16. The system of claim 1 wherein the imaging apparatus includes one or more of a confocal microscope and a brightview microscope.

17. The system of claim 1 wherein the imaging apparatus includes a laser that generates a beam suitable for one or more of ablation, photoactivation, and photostimulation.

18. The system of claim 1 wherein the system is used to perform genetic screens.

19. The system of claim 1 wherein the system is used to perform chemical screens.

20. An automated system for in vivo screens on vertebrate larvae comprising:
    a source of vertebrate larvae in a liquid medium;
    a pump configured to aspirate a larva in the liquid medium into a transparent tube;
    an automatic optical detection means to differentiate passage of the larva from bubbles or debris in the transparent tube;
    an imaging apparatus configured to image the larva in the transparent tube; and
    a motor and capillary assembly operable to rotate the transparent tube, thereby rotating the larva within a field of view of the imaging apparatus.

* * * * *